(12) United States Patent
Doty (10) Patent No.: US 7,457,661 B2
(45) Date of Patent: Nov. 25, 2008

(54) CATHETER-BASED, DUAL COIL PHOTOPOLYMERIZATION SYSTEM

(75) Inventor: David Doty, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 330 days.

(21) Appl. No.: 11/090,783

(22) Filed: Mar. 24, 2005

(65) Prior Publication Data

US 2006/0217653 A1    Sep. 28, 2006

(51) Int. Cl.
*A61N 1/30* (2006.01)
*A61B 18/18* (2006.01)

(52) U.S. Cl. .................. 604/21; 604/20; 606/2
(58) Field of Classification Search ............ 604/20, 604/21; 606/2
See application file for complete search history.

(56) References Cited

U.S. PATENT DOCUMENTS

| | | | | |
|---|---|---|---|---|
| 4,878,492 A | * | 11/1989 | Sinofsky et al. | 606/7 |
| 5,632,767 A | * | 5/1997 | Sinofsky | 607/89 |
| 5,779,673 A | * | 7/1998 | Roth et al. | 604/101.03 |
| 5,951,539 A | | 9/1999 | Nita et al. | |
| 5,964,751 A | * | 10/1999 | Amplatz et al. | 606/15 |
| 5,997,570 A | * | 12/1999 | Ligtenberg et al. | 607/92 |
| 6,245,040 B1 | * | 6/2001 | Inderbitzen et al. | 604/103.07 |
| 6,263,236 B1 | * | 7/2001 | Kasinkas et al. | 604/21 |
| 7,037,490 B2 | * | 5/2006 | Rowe et al. | 424/78.08 |
| 2002/0099332 A1 | | 7/2002 | Slepian et al. | |
| 2003/0032916 A1 | | 2/2003 | Rowe et al. | |

FOREIGN PATENT DOCUMENTS

WO   WO 90/01969   3/1990

OTHER PUBLICATIONS

Nguyen, Kytai Truong et al., "Photopolymerizable Hydrogels For Tissue Engineering Applications" Biomaterials 23 (2002) 4307-4314.

* cited by examiner

*Primary Examiner*—Nicholas D Lucchesi
*Assistant Examiner*—Victoria P Campbell

(57) ABSTRACT

A system for applying a polymer (hydrogel) to the inner surface of a vessel by photopolymerization includes an inner catheter received within an outer catheter and a fluid channeling structure mounted on the catheters with its proximal end attached to the outer catheter and its distal end attached to the inner catheter. The fluid channeling structure includes an elastomeric sleeve sandwiched between an inner elastic coil and an outer light emission coil. Light emission coil loops are interspaced with elastic coil loops. The light emission coil has a smaller diameter than the elastic coil, drawing the elastomeric sleeve down between loops of the elastic coil to form a helical channel. The coils and sleeve are stretched to provide a narrowed crossing profile for delivery, and are contracted at a treatment site to form a helical cavity between the sleeve and the vessel wall within which to perform interfacial photopolymerization.

11 Claims, 7 Drawing Sheets

CATHETER-BASED, DUAL COIL PHOTOPOLYMERIZATION SYSTEM

TECHNICAL FIELD

This invention relates generally to biomedical systems for treating vascular conditions. More specifically, the invention relates to a catheter-based, dual coil photopolymerization system.

BACKGROUND OF THE INVENTION

Photopolymerization, i.e., polymerization induced by light, is used to convert a liquid monomer or macromer to a polymer using visible or ultraviolet radiation. Some types of cross-linked hydrophilic polymers known as hydrogels may be formed in vivo using photopolymerization. These hydrogels exhibit good biocompatibility, making them attractive materials for use in a variety of biomedical applications.

Formation of photopolymerized hydrogels in vivo can be accomplished using bulk or interfacial photopolymerization. In bulk photopolymerization, a photoinitiator is dissolved in a hydrogel precursor (prepolymer) solution. A photoinitiator is a material that has a high absorption at a specific wavelength of light to produce radical initiating species that convert a prepolymer to a polymer. Upon exposure to an appropriate wavelength of light, the hydrogel precursor and photoinitiator solution is converted to the hydrogel state.

In interfacial photopolymerization, a photoinitiator is adsorbed onto the surface of tissues or cells. Eosin photoinitiators are commonly used because of their high affinity for tissues. A prepolymer, in this case a hydrogel precursor solution, is then delivered to the site, and the site is exposed to an appropriate light source. Polymerization occurs at the tissue interface, where the hydrogel precursor is in contact with the adsorbed photoinitiator.

Interfacial photopolymerization may be used to form thin hydrogel linings on various tissue surfaces, including the inner walls of vessels carrying bodily fluids. Dual occlusion catheters are currently used to deliver photoinitiators and prepolymers to target vessels. The treatment cavity formed between the two balloons must be filled with each component, requiring a relatively large amount of material. For example, typically about 3 milliliters of a prepolymer is required to fill the cavity, even though only a fraction of the material is converted into a hydrogel coating on the wall of the vessel. In addition, complications can occur if the vessel is occluded for more than 60 seconds. This may require the clinician performing the procedure to rush in order to avoid damage to the vessel and other complications when using a dual occlusion catheter.

Therefore, it would be desirable to have an improved catheter-based photopolymerization system and treatment method that overcome the aforementioned and other disadvantages.

SUMMARY OF THE INVENTION

One aspect of the present invention is a system for treating a vascular condition. The system comprises an outer catheter, an inner catheter, and a fluid channeling structure. A proximal portion of the inner catheter is slidably received within the outer catheter to form a catheter assembly. The fluid channeling structure is mounted on the catheter assembly with a proximal portion of the structure affixed to a distal portion of the outer catheter and a distal portion of the structure affixed to a distal portion of the inner catheter. The fluid channeling structure comprises an elastic coil, an elastomeric sleeve, and a light emission coil that has a diameter smaller than that of the elastic coil. The elastic coil is received within the elastomeric sleeve, and the elastomeric sleeve is received within the light emission coil. Loops of the light emission coil are interspaced with loops of the elastic coil.

Another aspect of the present invention is a method of assembling a system for treating a vascular condition. A catheter assembly is formed by positioning a proximal portion of an inner catheter within a lumen of an outer catheter. A fluid channeling structure is formed by positioning an elastic coil within an elastomeric sleeve and then coiling an optical fiber about the elastomeric sleeve. A distal portion of the catheter assembly is positioned within the fluid channeling structure. A proximal portion of the fluid channeling structure is attached to a distal portion of the outer catheter. A distal portion of the fluid channeling structure is attached to a distal portion of the inner catheter.

Yet another aspect of the present invention is a method of treating a vascular condition. A system for treating a vascular condition is delivered to a treatment site within a vessel. A distal portion of the system is expanded to form a helical cavity between the distal portion and an inner wall of the vessel. A fluid is delivered to the helical cavity. The helical cavity is exposed to light along a helical path.

The aforementioned and other features and advantages of the invention will become further apparent from the following detailed description, read in conjunction with the accompanying drawings, which are not to scale. The detailed description and drawings are merely illustrative of the invention rather than limiting, the scope of the invention being defined by the appended claims and equivalents thereof.

BRIEF DESCRIPTION OF THE DRAWINGS

Like reference numbers are used throughout the drawings to refer to like elements.

DETAILED DESCRIPTION

Figure 1:
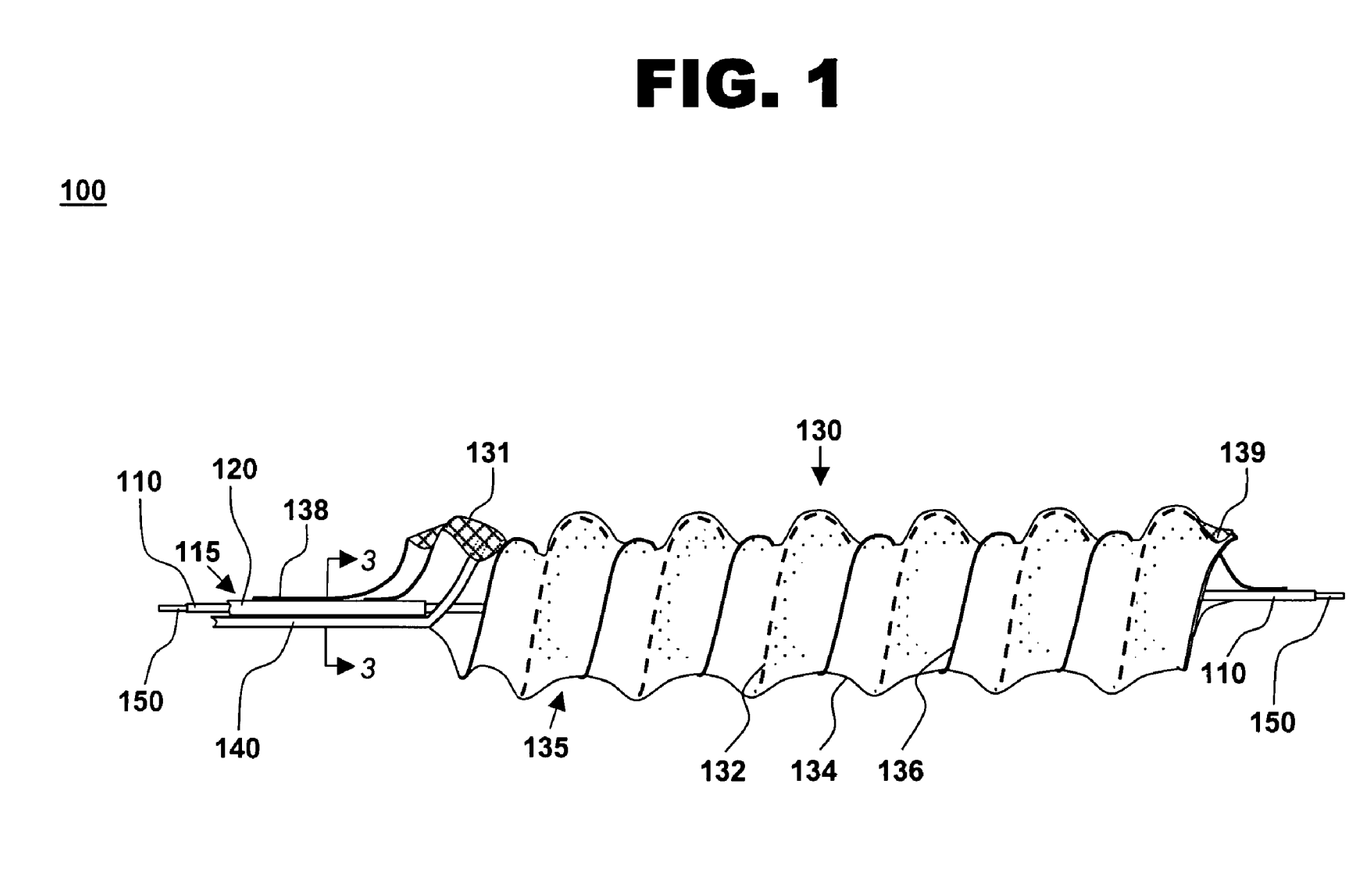
FIG. 1 is an illustration of one embodiment of a system for treating a vascular condition, in accordance with the present invention, showing the system as it would appear when deployed at a treatment site within a vessel.
Figure 2:
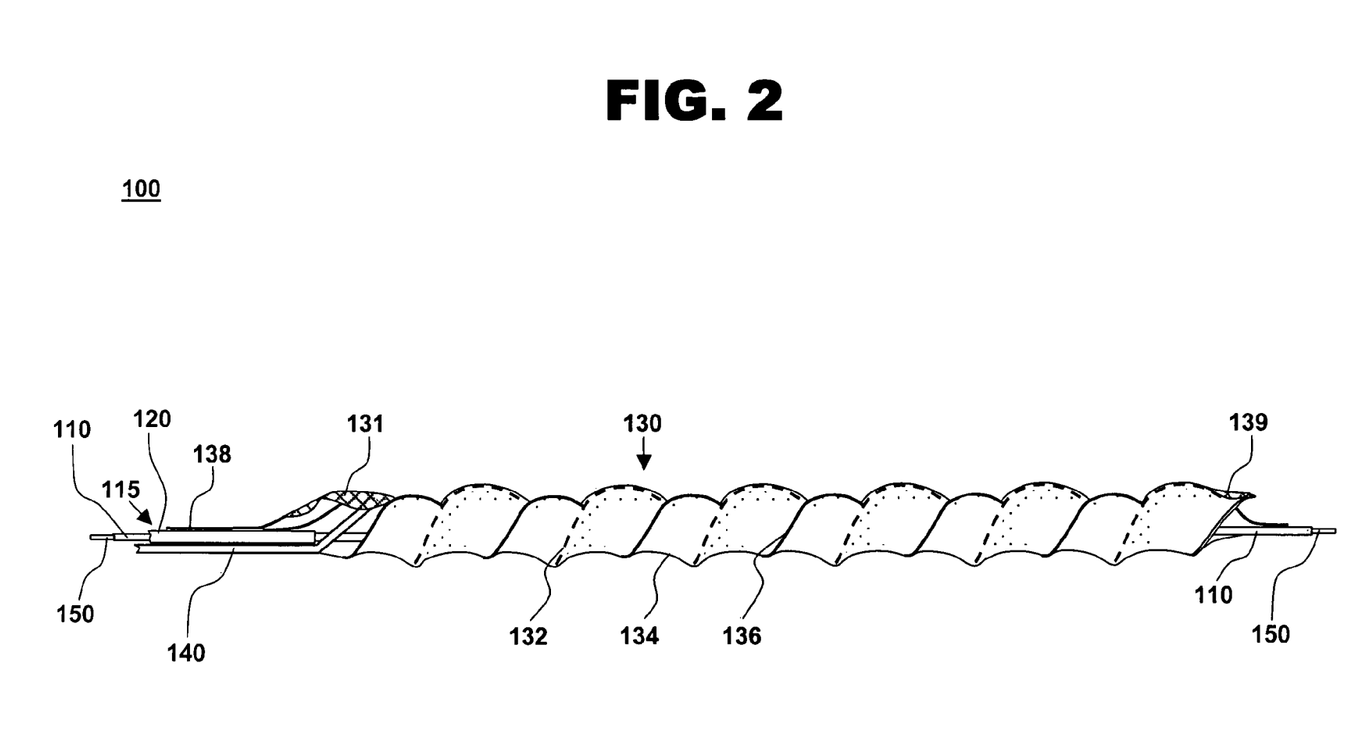
FIG. 2 is an illustration of the system of FIG. 1, showing the system having a narrowed crossing profile for delivery of the system to a treatment site within a vessel.

One aspect of the present invention is a system for treating a vascular condition. One embodiment of the system is illustrated at 100 in FIGS. 1 and 2. System 100 comprises an inner catheter, guidewire catheter 110; an outer catheter, pullback catheter 120; a fluid channeling structure 130; a fluid delivery catheter 140; and a guidewire 150. Guidewire catheter 110 and pullback catheter 120 combine to form a catheter assembly 115. Fluid channeling structure 130 includes an elastic coil 132, an elastomeric sleeve 134, and a light emission coil 136. FIG. 1 shows fluid channeling structure 130 as it would appear when expanded at a treatment site within a vessel. FIG. 2 shows fluid channeling structure 130 extended longitudinally to provide a narrowed crossing profile for delivery of system 100 to a target treatment area within a vessel.

Figure 3:
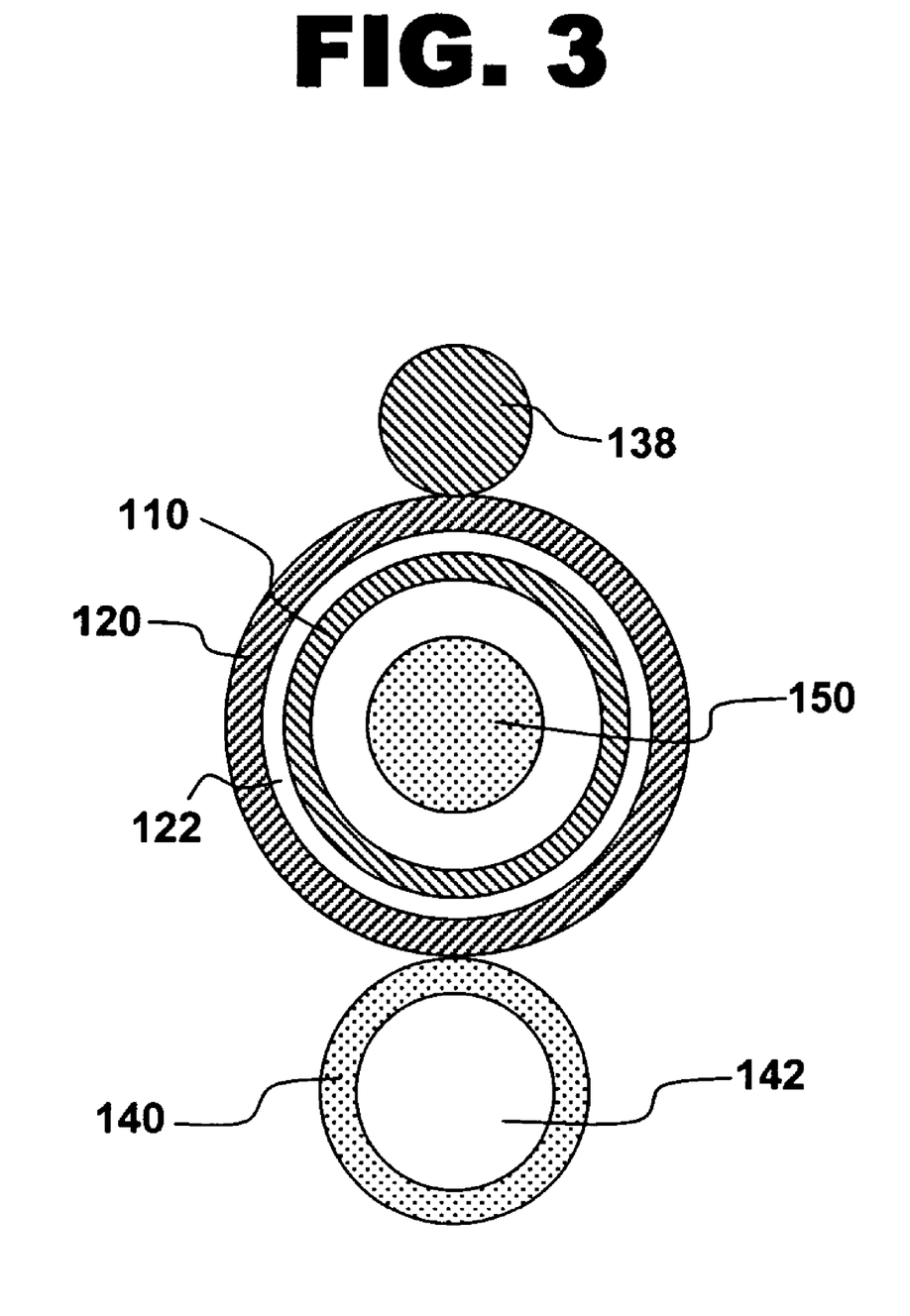
FIG. 3 is an enlarged cross-sectional view of a segment of the system of FIG. 1.

In the present embodiment, guidewire catheter 110 is a stainless steel hypotube. Other catheters may be used, including, but not limited to, catheters formed using nitinol, polyurethane, polytetrafluoroethylene (PTFE), polyethylene, and nylon. A distal portion of guidewire catheter 110 is spiral cut to provide increased flexibility. A proximal portion of guidewire catheter 110 is slidably received within central lumen 122 (shown in FIG. 3) of pullback catheter 120. Together, guidewire catheter 110 and pullback catheter 120 form catheter assembly 115.

Pullback catheter 120 comprises one or more biocompatible materials, including, but not limited to, polyurethane, polytetrafluoroethylene (PTFE), polyethylene, nylon, nitinol, and stainless steel. The distal tip of pullback catheter 120 may be necked down or thermally formed to reduce the diameter of the tip to create a partial seal with guidewire catheter 110. The partial seal minimizes blood flow between the pullback catheter and the guidewire catheter, as well as improves tractability, by reducing the gap between the two catheters. Pullback catheter 120 is so called because it is used to pull back on fluid channeling structure 130 to longitudinally extend the structure, thereby reducing the crossing profile of the fluid channeling structure for delivery to and withdrawal from a target treatment area within a vessel.

Fluid channeling structure 130 comprises elastic coil 132, elastomeric sleeve 134, and light emission coil 136. In the present embodiment, elastic coil 132 is a nitinol coil. In another embodiment, the elastic coil may be formed using another elastic material capable of being preset into a coiled configuration that is not significantly deformed by alternately stretching and compressing the coil. That is, the spacing between loops of elastic coil 132 remains substantially uniform whether the coil is stretched or compressed, and the coil is capable of self expanding into a deployment configuration having a predetermined diameter. Such materials include, but are not limited to, another nickel-titanium alloy, a nickel-cobalt alloy, another cobalt alloy, a thermoset plastic, stainless steel, a suitable biocompatible shape-memory material, a suitable biocompatible superelastic material, combinations thereof, and the like.

Elastic coil 132 (shown in phantom) is received within elastomeric sleeve 134. Elastomeric sleeve 134 is formed using one or more appropriate biocompatible materials. In the present embodiment, system 100 is used to apply a polymer coating (typically a hydrogel) to the inner surface of a vessel by interfacial photopolymerization using a photoinitiator. Therefore, the composition of elastomeric sleeve 134 is determined based on the polymer coating to be applied, with a composition chosen that does not absorb or otherwise retain the photoinitiator and that will not adhere to the coating material following photopolymerization of the prepolymer. For example, where the prepolymer to be applied is a bioresorbable polyethylene glycol (PEG) based polymer using a photoinitiator such as eosin-Y, elastomeric sleeve 134 may comprise a silicon or thermoplastic elastomer such as polyurethane. The term "prepolymer" is used herein to refer to any monomer, macromer, or polymer that is converted by photopolymerization in the presence of a photoinitiator to a polymer coating.

Elastomeric sleeve 134 is received within light emission coil 136. In the present embodiment, light emission coil 136 is formed into a distal portion of an optical fiber. This distal portion of the fiber is abraded to diffuse light from the coil. A proximal portion of the fiber, indicated at 138 in FIG. 1, is substantially straight and extends along the length of pullback catheter 120, terminating at a connecter arm of a luer (not shown). Light emission coil 136 is operably connected to a light source via proximal portion 138. In another embodiment, light emission coil 136 may be a section of optical fiber that is treated in another manner to diffuse light from the fiber. In still another embodiment, light emission coil 136 may be any material capable of emitting the desired intensity of light and may be operably connected to a light source by any means of conveying light to the coil. To aid in maintaining its coiled configuration, light emission coil 136 may be reinforced with a material such as nitinol or may comprise a glass/graphite reinforced plastic composite coil.

Light emission coil 136 is smaller in diameter than elastic coil 132. For example, where elastic coil 132 has a 3-millimeter outer diameter, light emission coil 136 will have an outer diameter between 2.5 and 2.75 millimeters. As can be seen in FIG. 1, loops of light emission coil 134 are interspaced with (i.e., positioned between) loops of elastic coil 132 and constrict elastomeric sleeve 134 within the loops of elastic coil 132 such that a helical channel 135 is formed in the sleeve when fluid channeling structure 130 is fully expanded as seen in FIG. 1.

Fluid channeling structure 130 is mounted on catheter assembly 115 such that a proximal portion of fluid channeling structure 130 is affixed to pullback catheter 120 and a distal portion of fluid channeling structure 130 is affixed to guidewire catheter 110. In the present embodiment, the distal end of elastic coil 132 is bonded or otherwise permanently attached to a distal portion of guidewire catheter 110. The proximal end of elastic coil 132 is similarly attached to a distal portion of pullback catheter 120. Elastomeric sleeve 134 is attached to elastic coil 132 by bonding or by adhesion of the elastomeric material to the coil. The sleeve is not attached to either guidewire catheter 110 or pullback catheter 120. The distal end of light emission coil 136 is embedded in or connected to elastomeric sleeve 134 adjacent to the distal end of elastic coil 132. Light emission coil 136 is secured or bonded at its proximal end to a distal portion of pullback catheter 120 and proximal portion 138 of the fiber optic wire runs the length of the pullback catheter and terminates at the appropriate connecter arm of a luer. In alternative embodiments, at least elastic coil 132 is affixed to both guidewire catheter 110 and pullback catheter 120. Elastomeric sleeve 134 and light emission coil 136 may be attached to one or both or neither of the catheters.

As seen in FIG. 2, system 100 is delivered to the target treatment area with pullback catheter 120 applying tension to (pulling back on) fluid channeling structure 130 such that elastic coil 132 is extended longitudinally, thereby reducing the diameter of the elastic coil. This, in turn, reduces the diameter of light emission coil 136 and elastomeric sleeve 134 and minimizes the crossing profile of system 100. For example, a system having an expanded profile of 3 millimeters may be reduced for delivery to a longitudinally extended profile of 1 to 2 millimeters. The proximal end of pullback catheter 120 may include a locking mechanism to ensure the relative positions of guidewire catheter 110 and pullback catheter 120 remain fixed throughout delivery of system 100 to the target treatment area, thereby maintaining the system in its minimized crossing profile.

System 100 is deployed at the target treatment area by retracting guidewire catheter 110 while pullback catheter 120 and guidewire 150 remain stationary. The proximal end of guidewire catheter 110 may terminate in a telescoping, syringe-like or turnbuckle-like apparatus that allows guidewire catheter 110 to retract without changing the position of guidewire 150. As guidewire catheter 110 is retracted, elastic coil 132 self-expands into its preset deployment configuration having a predetermined diameter. The deployment diameter of elastic coil 132 may be varied somewhat by retracting guidewire catheter 110 to a distance that does not permit full expansion of the elastic coil, thereby producing a diameter smaller than the fully self-expanded diameter, or by retracting catheter 110 such that elastic coil becomes longitudinally compressed, thereby producing a diameter somewhat larger than the diameter achieved by self-expansion of elastic coil 132. For example, in a system having a self-expanded profile of 3 millimeters, the variation in diameter may range from about 2.5 to about 5 millimeters. The expanding elastic coil 132 also expands light emission coil 136 and elastomeric sleeve 134 to form helical channel 135.

When fluid channeling structure 130 is expanded within a vessel, helical channel 135 forms a helical cavity between the outer surface of fluid channeling structure 130 and the inner wall of the vessel. Individual loops of elastic coil 132 are compressible to allow fluid channeling structure 130 to exert minimal pressure on the wall of the vessel while still conforming to indentations and protrusions in the inner wall of the vessel at the target treatment area. Once fluid channeling structure 130 is fully expanded, the bodily fluid carried within the vessel is able to flow freely through the center of the structure. Thus, the flow of the bodily fluid is minimally impeded during treatment, with the fluid flowing around an undeployed fluid channeling structure during positioning of the system and flowing through the center of a fully expanded fluid channeling structure.

A proximal dam 131, for example a buildup of elastomeric material at the proximal end of elastic coil 132 or one or two complete wraps of elastic coil 132, acts as a fluid barrier to fully seal the helical cavity at the proximal end of fluid channeling structure 130. Proximal dam 131 prevents fluid from exiting fluid channeling structure 130 at the proximal end of the structure. A distal dam 139, for example a buildup of elastomeric material at the distal end of elastic coil 132, acts as a fluid barrier to partially seal the helical cavity at the distal end of fluid channeling structure 130 while still allowing fluid to pass beyond the dam as pressure builds up within the helical cavity. Thus, distal dam 139 creates backpressure, ensuring the helical cavity becomes filled with a fluid but allowing a minimal amount of fluid to exit the distal end of fluid channeling structure 130 as needed.

Fluid channeling structure 130 is in fluid communication with one or more fluid supplies via fluid delivery catheter 140. Fluid delivery catheter 140 runs parallel to pullback catheter 120 and is affixed to pullback catheter 120 by, for example, enclosing the catheters in ultra-thin heat-shrink tubing along the length of the catheters or at spaced intervals along the length of the catheters. The relative positioning of guidewire catheter 110, pullback catheter 120, and fluid delivery catheter 140 can be best seen in FIG. 3, which shows an enlarged cross-sectional view of a distal segment of system 100.

In the present embodiment, in which system 100 is used to apply a polymer coating to the inner surface of a blood or other vessel by interfacial photopolymerization using a photoinitiator, fluid channeling structure 130 is in fluid communication with supplies of a photoinitiator and a prepolymer via fluid delivery lumen 142. A valve or manifold system (not shown) at the proximal end of system 100 is used to deliver the appropriate fluid to the proximal end of fluid delivery lumen 142 at any given time. The fluid exits the distal end of fluid delivery lumen 142 and flows through fluid channeling structure 130 until the cavity formed between the fluid channeling structure and the vessel wall is completely filled, with the fluid flowing into fluid channeling structure 130 at the proximal end of the structure and a small amount of excess flowing out the distal end of the structure, past distal dam 139.

Fluid delivery catheter 140 is also in fluid communication with a supply of a saline or other flushing solution to permit flushing of either or both of fluid delivery lumen 142 and the helical cavity. Once the photoinitiator in contact with the vessel wall is adsorbed on (or is otherwise bound to) the tissue of the vessel wall, excess photoinitiator is flushed from the cavity prior to delivering the prepolymer.

Figure 4:
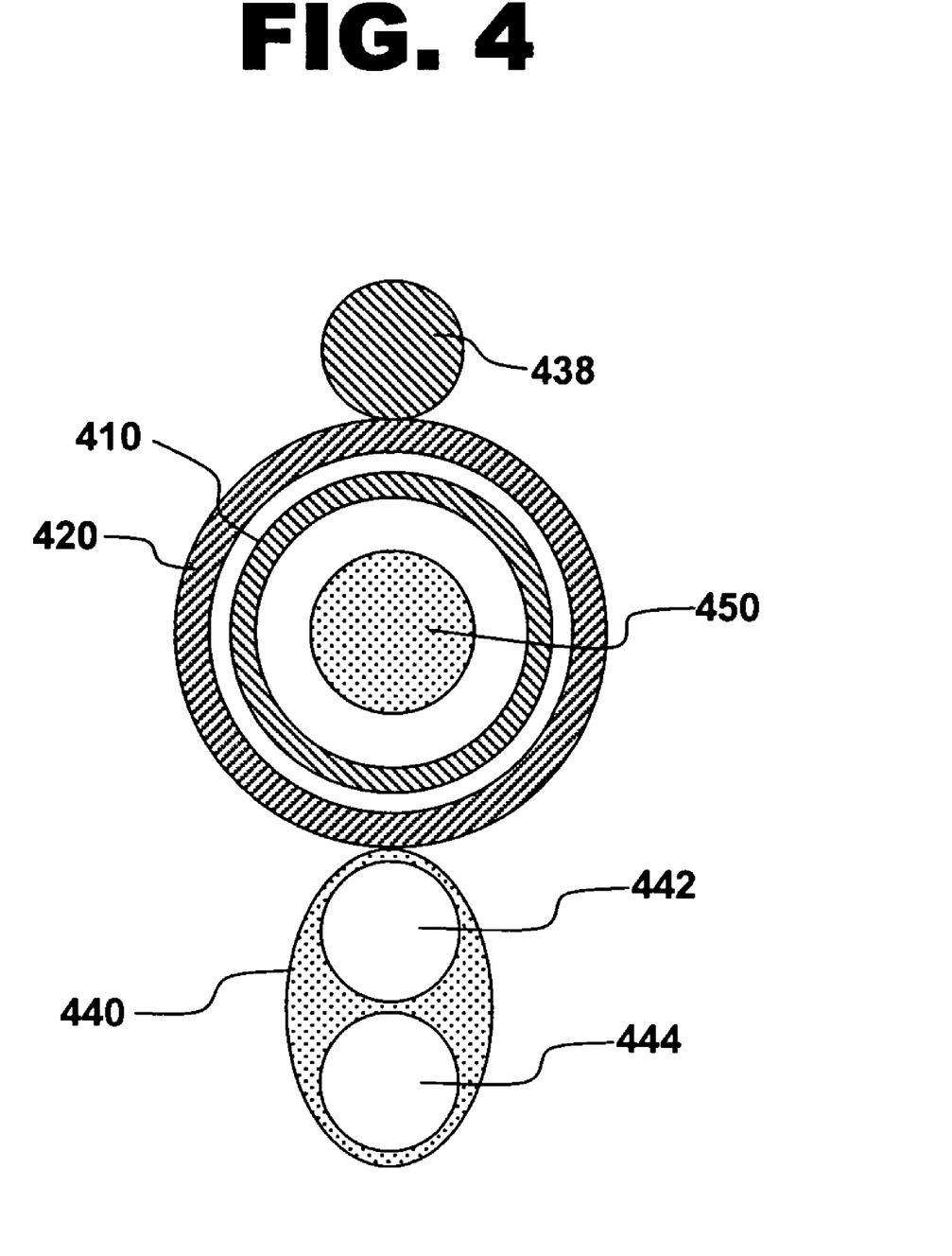
FIG. 4 is a cross-sectional view of a segment of another embodiment of a system for treating a vascular condition, in accordance with the present invention.

In an alternative embodiment, a proximal segment of which is seen in cross-section in FIG. 4, the fluid delivery catheter 440 may be configured with both a fluid delivery lumen 442 and a separate flushing lumen 444. This design permits flushing of the helical cavity following delivery of the photoinitiator without having to flush additional photoinitiator that remains in the fluid delivery lumen into the vessel, thereby minimizing the amount of photoinitiator that enters the vessel. The two lumens may be fully separate, or the lumens may bifurcate proximal to a distal common tip. In an embodiment having a separate flushing lumen, the prepolymer may be delivered through the flushing lumen rather than through the fluid delivery lumen. The positioning of guidewire catheter 410, pullback catheter 420, fiber optic wire 438, and guidewire 450 is similar to that of system 100.

Figure 5:
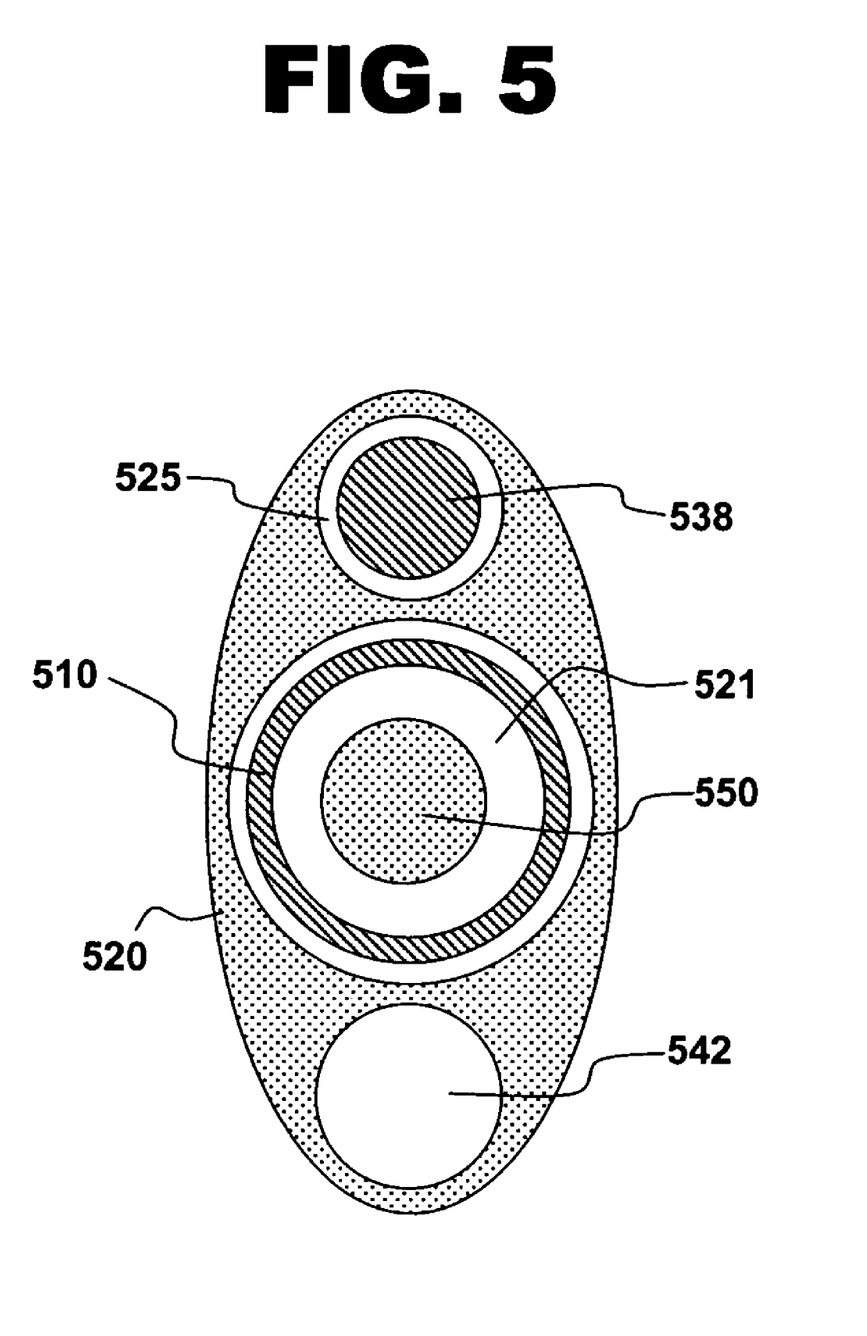
FIG. 5 is a cross-sectional view of a segment of yet another embodiment of a system for treating a vascular condition, in accordance with the present invention.

FIG. 5 shows a cross-sectional view of a proximal segment of another alternative embodiment of a system for treating a vascular condition. In this embodiment, the system does not include a fluid delivery catheter. Instead, pullback catheter 520 contains not only a lumen 521 to receive guidewire catheter 510, but also a fluid delivery lumen 542. In this embodiment, fiber optic wire 538 is contained within pullback catheter 520 as well, running through a wire lumen 525, rather than being affixed to an outer surface of the pullback catheter as in system 100. A conduit may be joined to the proximal end of fluid delivery lumen 542 to direct fluids from lumen 542 into the helical channel formed in the fluid channeling structure of this embodiment.

Once the photoinitiator has been delivered to helical channel 135 and unbound photoinitiator has been flushed from the channel, prepolymer is delivered to the channel until it fills the cavity formed between the channel and the vessel wall. The light source operably connected to light emission coil 136 is then activated, causing the coil to deliver light to the vessel wall, thereby curing the prepolymer and forming a polymer (typically a hydrogel) coating on the wall of the vessel. Fluid channeling structure 130 may then be returned to its reduced crossing profile by extending guidewire catheter 110 within a stationary pullback catheter 120. Uncured material will be washed away as fluid channeling structure 130 contracts away from the wall of the vessel. Alternatively, uncured material may be removed prior to contracting fluid channeling structure 130 by, for example, pulling a vacuum on fluid delivery catheter 140.

In practice, a system in accordance with the present invention significantly reduces the amount of photoinitiator and prepolymer used in treating a vessel. Because the fluid must fill only the helical cavity between the fluid channeling structure and the wall of the vessel, rather than the entire lumen of the vessel, less than a milliliter of fluid is needed. Further, the flow of a bodily fluid through the vessel is not blocked during treatment, reducing the risk of damage to the vessel and eliminating the need to rush the treatment procedure in order to return flow through the vessel as quickly as possible.

One skilled in the art will appreciate that, while described above in the context of forming a coating on the inner surface of a vessel, the system may be used for other applications. For example, a coating may be formed on all or part of the inner surface of a treatment device such as a stent or graft positioned within the vessel, or on an inner surface of at least a portion of both the vessel and a treatment device. Further, the system may be used to deliver and activate materials other than photopolymerization materials, including, but not limited to, a photoactivated drug or other therapeutic agent.

Figure 6:
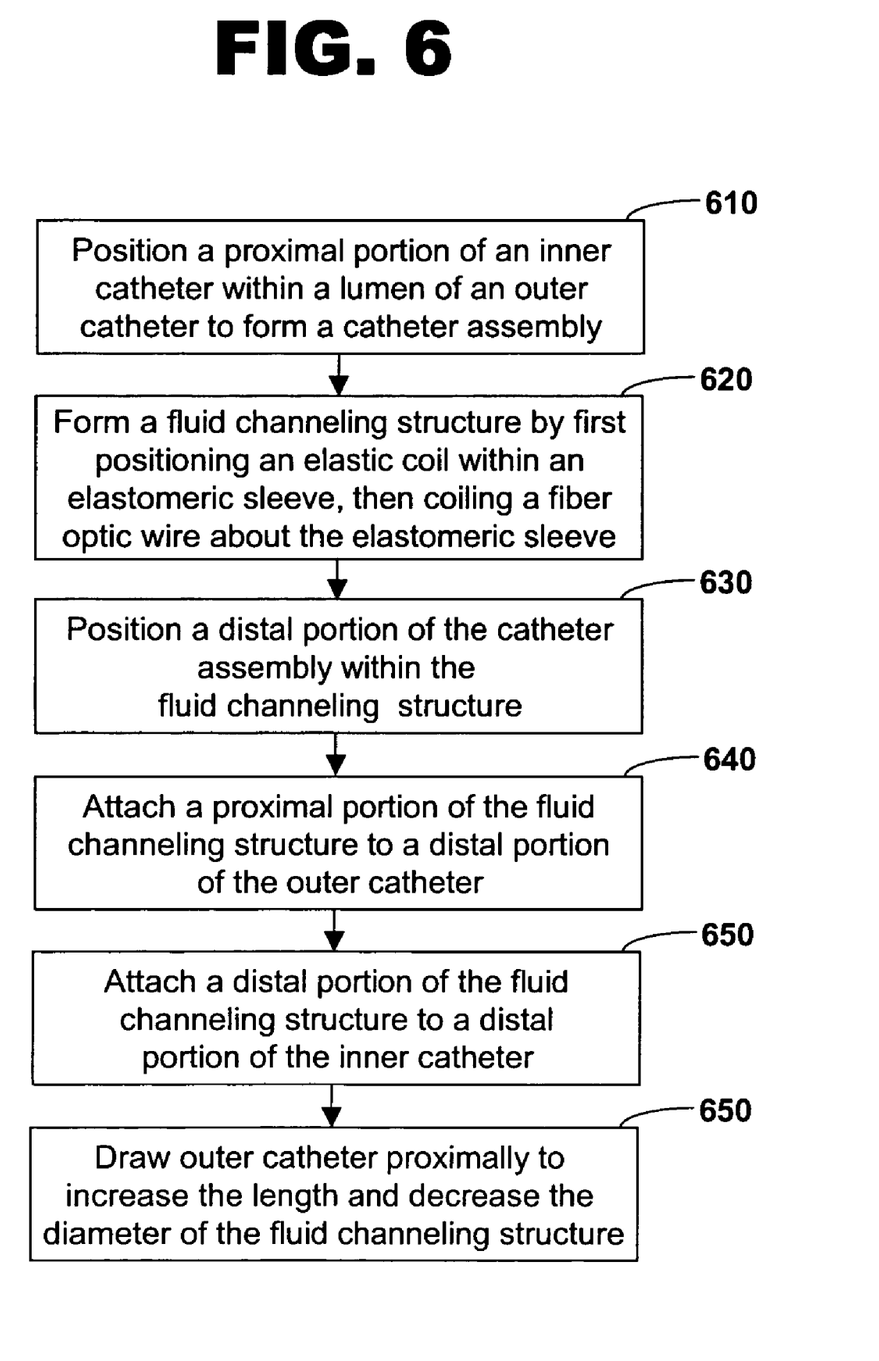
FIG. 6 is a flow diagram of one embodiment of a method of assembling a system for treating a vascular condition, in accordance with the present invention.

Another aspect of the present invention is a method of assembling a system for treating a vascular condition. FIG. 6 shows a flow diagram of one embodiment of the method in accordance with the present invention.

A catheter assembly is formed by positioning a proximal portion of an inner catheter within a lumen of an outer catheter (Block 610). The inner catheter may be threaded through the lumen of the outer catheter such that a distal portion of the inner catheter extends from the distal end of the outer catheter. A proximal portion of the inner catheter may extend from the proximal end of the outer catheter as well.

A fluid channeling structure is formed by positioning an elastic coil within an elastomeric sleeve and then coiling a fiber optic wire about the elastomeric sleeve (Block 620). The fiber optic wire is wrapped tightly about the elastomeric sleeve to form a fiber optic coil that has a diameter smaller than that of the elastic coil. Loops of the fiber optic coil are interspaced with (i.e., positioned between) loops of the elastic coil and constrict the elastomeric sleeve between loops of the elastic coil such that a helical channel is formed in the sleeve.

A distal portion of the catheter assembly is positioned within the fluid channeling structure (Block 630). This may be accomplished by threading the substantially tubular fluid channeling structure over the distal end of the catheter assembly until a proximal end of the fluid channeling structure is positioned over a distal portion of the outer catheter and a distal end of the fluid channeling structure is positioned over a distal portion of the inner catheter.

A proximal portion of the fluid channeling structure is attached to a distal portion of the outer catheter (Block 640). For example, a proximal portion of the elastic coil may be bonded or otherwise permanently attached to a distal portion of the outer catheter. A proximal portion of one or both of the elastomeric sleeve and the fiber optic coil may be similarly affixed to the outer catheter.

A distal portion of the fluid channeling structure is attached to a distal portion of the inner catheter (Block 650). A distal portion of the elastic coil may be bonded or otherwise permanently attached to a distal portion of the inner catheter. A distal portion of one or both of the elastomeric sleeve and the fiber optic coil may be similarly affixed to the inner catheter.

The outer catheter is drawn proximally such that the length of the fluid channeling structure is increased and the diameter of the fluid channeling structure is decreased (Block 660). Because a distal portion of the fluid channeling structure is affixed to the inner catheter, while a proximal portion of the structure is affixed to the outer catheter, pulling the outer catheter in a proximal direction extends the elastic coil longitudinally, thereby reducing the winding diameter of the coil, while at the same time extending and narrowing both the light emission coil and the elastomeric sleeve. The proximal end of the catheter assembly may include a locking mechanism to ensure the relative positions of the inner and outer catheters remain fixed throughout delivery of the system to a target treatment area, thereby maintaining the system in an extended and minimized crossing profile.

Figure 7:
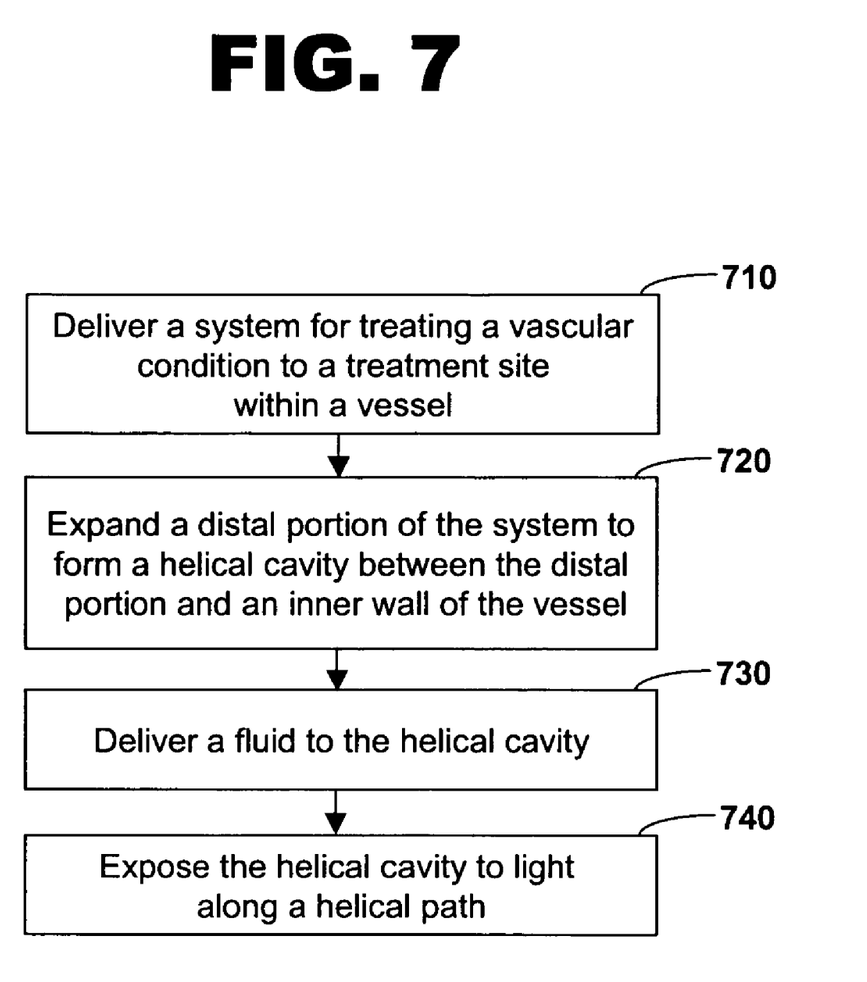
FIG. 7 is a flow diagram of one embodiment of a method of treating a vascular condition, in accordance with the present invention.

Yet another aspect of the present invention is a method of treating a vascular condition. FIG. 7 shows a flow diagram of one embodiment of the method in accordance with the present invention.

A system for treating a vascular condition is delivered to a treatment site within a vessel (Block 710). For example a system such as is described above and illustrated in FIGS. 1 and 2 at 100 may be delivered to a target treatment area within a blood vessel.

A distal portion of the system is expanded to form a helical cavity between the distal portion and an inner wall of the vessel (Block 720). This may be accomplished as described previously, with fluid channeling structure 130, positioned adjacent to a distal end of system 100, being expanded within a vessel to form a helical cavity 135 between the fluid channeling structure and the inner wall of the vessel.

A fluid is delivered to the helical cavity (Block 730). For example, a prepolymer may be delivered to the cavity after a photoinitiator has been adsorbed on (or otherwise bound to) the inner wall of the vessel. Both the photoinitiator and the prepolymer may be delivered to fluid channeling structure 122 via fluid delivery catheter 140. Excess photoinitiator may be flushed from the cavity using a saline or other flushing solution prior to delivery of the prepolymer.

The helical cavity is exposed to light along a helical path (Block 740). In the present example, light is conveyed to light emission coil 136 via the proximal portion of the fiber optic wire used to form light emission coil 136, the proximal portion being indicated at 138 in FIGS. 1 and 2. The light forms a helical path defined by the loops of light emission coil 136. As the light is emitted by the coil, the prepolymer within the helical cavity is cured or polymerized to form a polymer (typically a hydrogel) coating on the inner wall of the vessel. Fluid channeling structure 130 may then be returned to its reduced crossing profile for withdrawal of the system from the vessel.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for treating a vascular condition, comprising:
   an outer catheter;
   an inner catheter having a proximal portion and a distal portion, the proximal portion slidably received within the outer catheter to form a catheter assembly; and
   a fluid channeling structure mounted on the catheter assembly such that a proximal portion of the structure is affixed to the outer catheter and a distal portion of the structure is affixed to the inner catheter, the delivery structure comprising an elastic coil, an elastomeric sleeve, and a light emission coil having a diameter smaller than that of the elastic coil, wherein the elastic coil is received within the elastomeric sleeve, and the elastomeric sleeve is received within the light emission coil, and wherein loops of the light emission coil are interspaced with loops of the elastic coil.

2. The system of claim 1 wherein the loops of the light emission coil interspaced with the loops of the elastic coil form a helical channel in the elastomeric sleeve.

3. The system of claim 1 wherein the fluid channeling structure further comprises:

a proximal fluid barrier; and a distal fluid barrier.

4. The system of claim 1 wherein the fluid channeling structure is in fluid communication with at least one fluid supply.

5. The system of claim 4 wherein the fluid supply is a supply of a photoinitiator.

6. The system of claim 4 wherein the fluid supply is a supply of a prepolymer.

7. The system of claim 1 wherein the outer catheter includes a lumen.

8. The system of claim 1 further comprising:

a fluid delivery catheter.

9. The system of claim 8 wherein the fluid delivery catheter includes a fluid delivery lumen and a flushing lumen.

10. The system of claim 1 wherein the light emission coil is operably connected to a light source.

11. The system of claim 10 wherein the outer catheter includes a lumen through which the light emission coil is operably connected to a light source.

* * * * *